United States Patent [19]

Hattori et al.

[11] Patent Number: 4,540,416

[45] Date of Patent: Sep. 10, 1985

[54] HEAT-STERILIZABLE POLYOLEFIN COMPOSITIONS AND ARTICLES MANUFACTURED THEREFROM

[75] Inventors: Kiyoshi Hattori, Franklin Lakes, N.J.; John H. Myers, Swarthmore, Pa.

[73] Assignee: El Paso Polyolefins Company, Odessa, Tex.

[21] Appl. No.: 687,408

[22] Filed: Dec. 28, 1984

Related U.S. Application Data

[60] Division of Ser. No. 524,114, Aug. 18, 1983, , which is a continuation-in-part of Ser. No. 469,881, Mar. 3, 1983, abandoned, which is a continuation-in-part of Ser. No. 450,948, Dec. 20, 1982, abandoned.

[51] Int. Cl.³ ...................... B65B 25/00; C08L 23/16; C08L 23/18
[52] U.S. Cl. ........................... 604/410; 128/DIG. 24; 525/240
[58] Field of Search ......................... 525/240; 604/410

[56] References Cited

U.S. PATENT DOCUMENTS

| | | | |
|---|---|---|---|
| 3,254,139 | 5/1966 | Anderson et al. | 525/240 |
| 4,335,224 | 6/1982 | Matsuura et al. | 525/240 |
| 4,395,519 | 7/1983 | Minami et al. | 525/240 |
| 4,434,264 | 2/1984 | Ficker | 524/323 |

FOREIGN PATENT DOCUMENTS 0052557  5/1982  European Pat. Off. .

*Primary Examiner*—Carman J. Seccuro
*Attorney, Agent, or Firm*—Fred S. Valles; Margareta LeMaire

[57] ABSTRACT

Heat-sterilizable films are made from a polymer blend of about 10 to about 60 wt % random propylene-ethylene copolymer containing from about 1 to about 6 wt % ethylene-derived units and about 40 to about 90 wt % linear low density polyethylene. The films are especially useful in the manufacture of collapsible parenteral solution bags and overwraps.

12 Claims, No Drawings

HEAT-STERILIZABLE POLYOLEFIN COMPOSITIONS AND ARTICLES MANUFACTURED THEREFROM

This is a division of application Ser. No. 524,114, filed Aug. 18, 1983, which is a continuation-in-part of application Ser. No. 469,881 filed Mar. 3, 1983, now abandoned, which is a continuation-in-part of application Ser. No. 450,948, filed Dec. 20, 1982, now abandoned.

BACKGROUND OF THE INVENTION

Parenteral solutions broadly cover fluid replacement, electrolyte replacement and are vehicles for drug medication. Solutions include blood plasma, platelets, red cells, kidney dialysis solutions, saline solutions and nutritional products. These solutions were initially bottled in glass, however, with the introduction of the collapsible parenteral solution bag some years ago, airborne contamination was significantly reduced since the flexible bags empty without outside air entering the system.

The general requirements of a resin used in the manufacture of the parenteral solution bags include flexibilty, clarity, toughness at low temperatures, heat sealability, good processability, moisture vapor permeability resistance and ability to be sterilized. The industry is presently employing a highly plasticized PVC film for this purpose. Although this resin does meet most of the requirements, a material is preferred that has little or no plasticizer. Also the PVC film is not very resistant to moisture vapor permeability, and consequently, the continuing loss of moisture of the parenteral solutions reduces their storage life considerably. Therefore, it is required that the bag be sealed within an overpouch made from a film resin designed to have a low water vapor transmission rate (WVTR). Currently the overpouch film is made from a blend of high density polyethylene and butyl rubber and been extruded into film of a thickness of about 4–5 mil to provide the necessary WVTR. This thickness is usually more than needed for physical strength and adds to the cost of the assembly. Another drawback of the overpouch resin is that it lacks the desired clarity, an important property needed for easy and correct identification of the contents of the inner bag.

It is therefore an object of the present invention to provide a resin formulation which is suitable in the manufacture of sterilizable overpouch films of improved clarity and moisture vapor permeability resistance.

It is also an object of the present invention to provide a film useful in the manufacture of sterilizable, collapsible bags for direct and for indirect containment of parenteral solutions.

It is a further object of the invention to provide an improved collapsible intravenous bag assembly.

Other objects are readily determined from a reading of the specification and claims.

THE INVENTION

In accordance with the present invention there is provided a sterilizable film resin composition which comprises a blend of:
 (a) from about 10 to about 60 wt % of a random copolymer of from about 1 to about 6 wt % ethylene and from about 94 to about 99 wt % propylene;
 (b) from about 40 to about 90 wt % of a linear low density polyethylene produced by copolymerization of ethylene and at least one $C_4$–$C_{18}$ alpha-olefin and having a density between about 0.915 and about 0.940 gm/cc.

The random copolymer component preferably has a melt flow in the range between about 1.0 and about 5.0 g/10 min at 230° C. Such polymers are readily available commercially and their preparation need not therefore be discussed.

The linear low density polyethylene component, hereinafter sometimes identified as LLDPE, is an interpolymer of ethylene and at least one $C_4$–$C_{18}$ alpha-olefin in comonomer. Preferably the alpha-olefin comonomer contains from 4 to 8 carbon atoms per molecule. Examples of especially suitable comonomers are butene-1, pentene-1, hexene-1, 4 methyl-pentene-1, heptene-1, octene-1 and mixtures thereof such as butene-1/hexene-1 and butene-1/octene-1, etc. These LLDPE resins can be produced by any of the recently introduced catalytic processes using vapor, solution or slurry techniques at low to medium pressures or high pressure catalytic polymerization in autoclave or tubular reactors. The resin preferably has a melt index from about 0.5 to about 5 g/10 min. at 190° C. A variety of suitable resins are commercially available within the required density and melt flow ranges.

One optional component of the resin blend is an agent added in a quantity effective to produce films of improved clarity. Examples of suitable agents are sodium benzoate, dibenzylidene sorbitol, sorbitan monooleate and others. Usually the agents are added in quantities between about 0.1 and about 2 wt % based on the weight of the total polymers.

Also, from about 2 to about 15 wt% of a high density polyethylene, i.e., a homopolymer of ethylene having a density of at least 0.945 gm/cc can be included in the resin as another optional ingredient for the purpose of increasing the heat seal range. This property is defined as the time span between the minimum time to make a good seal and the maximum time before the film burns through employing a standard heat-sealing device.

The blend composition of the present invention is easily processable into blown or cast film products which, in addition to high clarity, exhibit other desirable properties such as flexibility, toughness at low temperatures, heat sealability. Also, the films have good resistance to moisture vapor permeability and can be steam sterilized at 121° C., without significantly affecting its physical properties in a detrimental way. Finally, the films contain no additives, which would prevent their use in food or medical applications, either in direct or indirect contact.

When used for an inner parenteral solution container, the film should have a thickness in the range of from about 3 to about 10 mils, while the overpouch need not be more than from about 1 to about 6 mils thick. If desired, co-extruded films for either the inner bag or the outer bag can be used to reduce loss of moisture or gases through the film walls. Materials such as fluorocarbon polymers, ethylene-vinyl alcohol copolymers and polyvinylidene chloride materials are examples of suitable co-extrudates.

Further improvements result from an overall parenteral solution bag assembly which comprises an inner sealed film bag containing the parenteral solution, an outer sealed film bag containing a small amount of water and enclosing the inner bag said outer bag having a width and a length of from about 0.25 to about 1.5 inches larger than the corresponding dimensions of the inner bag, the outer film resin comprising a blend of:
  (a) from about 10 to about 60 wt % of a random copolymer of from about 1 to about 6 wt % ethylene and of from about 94 to about 99 wt % propylene;
  (b) from about 40 to about 90 wt % of a linear low density produced by copolymerization polyethylene of ethylene and at least one $C_4$-$C_{18}$ alphaolefin and having a density between about 0.915 and about 0.940 gm/cc.

In one embodiment the small amount of water is added directly to the outer pouch before the sealing operation is carried out to enclose the inner bag. In another embodiment the small amount of water is enclosed in a separate smaller pouch manufactured from two film layers. For economic reasons, one of the films is suitably made from the same resin as that of the outer bag, while the other layer should be made from a porous material that allows vapor escape but is resistant to liquid permeability. Suitable materials for this purpose are commercially available, e.g., the Tyvek TM spunbonded polyethylenes available from E. I. DuPont deNemours. Moisture vapor is thereby permitted to escape from the small pouch more rapidly than from the outer bag, thus producing a saturated atmosphere between the inner and outer bag, effectively eliminating the driving force for water to escape from the inner bag and reducing the rate at which water vaporizes and leaves the inner bag. The area of one side of the smaller pouch should not exceed about 50% of the corresponding inner bag area.

The actual amount of water to be used to inhibit removal of water vapor from the inner bag should at least be sufficient to ensure that liquid water still be present in the space between the inner and outer bags at the expiration date of the parenteral solution. This amount will obviously vary from case to case and depends on the maximum allowable storage life of the parenteral solution, the size of the outer bag and the water vapor transmission rate through said bag.

An additional feature of this invention is the ability to substitute materials other than water in the small pouch. For example, a carbon dioxide absorber can be sealed in the small pouch and help in removing carbon dioxide from the inner bag or an oxygen generator can be added to aid in adding oxygen to the inner bag, thereby considerably increasing blood platelet storage life. Other materials and gases could also be handled and controlled in this manner in order to improve the storage performance of the system.

The use of the small pouch inserted in the space between the inner and outer bags simplifies all packaging operations to a large degree. Only one film material and thickness would be required for manufacturing and inventorying the inner bag for all types of solutions. Additionally, all outer bags can be of the same resin formulation and of one film thickness. Only different small pouches, identifiable, e.g., by color coding, need to be added.

In case the materials packaged in the inner bag are sensitive to ultra violet light, a small amount of an ultra violet screening agent can be incorporated in the outer bag which would prevent U.V. light from reaching the packaged products.

The film compositions are also high energy radiation sterilizable.

Also, either or both of the bags of the parenteral solution bag assembly may be manufactured from other polymer film compositions, provided that they are sterilizable by heat or irradiation and meet the general requirements of flexibility, toughness, heat sealability, etc., previously discussed.

To further illustrate the invention the following example is provided:

EXAMPLES 1

A resin blend containing 84.75 parts LLDPE (copolymer of ethylene and butene-1, density 0.918 g/cc, melt index 1.0 g/10 min), 15 parts random copolymer of 97.5% propylene and 2.5% ethylene (density 0.900 g/cc, melt flow 2.0 g/10 min). 0.25 parts dibenzylidene sorbitol was used in preparing blown films of 2.5 mil and 4.5 mil thicknesses. The resulting films had good clarity, toughness, were easily heat sealable and flexible. Pouches were made from these films, filled with water, heat sealed and tossed in the air to simulate a 10 foot drop. All pouches survive at least 6 drops at ambient temperatures (65° F.). The moisture vapor transmission rate of the films were approximately 0.7 grams/mil/100 square inches/24 hours.

Other test samples consisting of 5"×11" inner bags were prepared from the 4.5 mil film. These were filled with 1000 cc. water and enclosed in 6"×12" outer bags of the 2.5 mil film. A portion of the samples were provided with 70 cc water between the inner and outer bags. All of the samples passed the steam sterilization test carried out in an autoclave at 121° C. for 60 minutes.

Equally good results were obtained in experiments with films made from a resin blend similar in all aspects to the previous one except the LLDPE/copolymer weight ratio was changed from about 85:15 to about 60:40.

EXAMPLE 2

5 mil films were made from resins containing varying amounts of high density polyethylene (0.952 gm/cc) in addition to the LLDPE and the propyleneethylene random copolymer used in Example 1. Strips of two layers of these films were placed in an air oven at 250° F. for ½ to 1 hour. The strips were then taken out and inspected for any tendency to stick to itself. These same films were then tested in a heat sealing device to determine their ability to be heat sealed. An impulse type sealer made by Sentinel Industries weas used for these tests. The heating cycle was varied (in seconds) and the cooling time (4 sec.) and air pressure (21 psig) was held constant. The minimum time to make a good seal and the maximum time before the film burned through were determined and the time difference was the sealing range. Table 1 summarizes the data from these experiments.

As seen from the results, the addition of small amounts of high density polyethylene greatly increased the heat seal range.

Peel tests also showed that the seals were considerably stronger in films made from resins containing high density polyethylene as a third resin component. Other film properties were not adversely affected by this inclusion.

TABLE 1

| Test | Contr. 1 | A | B | C | D | E |
|---|---|---|---|---|---|---|
| $C_3{=}/C_2{=}$ copolymer wt % | — | 40 | 40 | 40 | 35 | 36 |

TABLE 1-continued

| Test | Contr. 1 | A | B | C | D | E |
|---|---|---|---|---|---|---|
| LLDPE wt % | 100 | 60 | 54 | 50 | 60 | 54 |
| HDPE wt % | — | — | 6 | 10 | 5 | 10 |
| Oven Test[1] | STICK | DNS | DNS | DNS | DNS | DNS |
| Heat Seal Range, Sec. | 2.5 | 1.3 | 1.8 | 2.3 | 2.4 | 2.4 |

[1]DNS — Did not stock - slight tackiness

It is to be understood that many modifications and alterations can be made to this invention without departing from its scope, which is defined by the specification and appended claims.

What is claimed is:

1. A sterilizable parenteral solution bag assembly comprising
   an inner sealed plastic film bag containing a parenteral solution;
   an outer sealed bag enclosing the inner bag, said outer bag having a width and a length from about 0.25 to about 1.5 inches larger than the corresponding dimensions of the inner bag; the outer film bag resin comprising a blend of:
   (a) from about 10 to about 60 wt % of a random copolymer of from about 1 to about 6 wt % ethylene and of from about 94 to about 99 wt % propylene;
   (b) from about 40 to about 90 wt % of a linear low density polyethylene produced by copolymerization of ethylene with at least one $C_4$–$C_{18}$ alpha-olefin comonomer and having a density between about 0.915 and about 0.940 gm/cc,
   in the space between the outer and inner bags a quantity of a substance sufficient to control removal of a component from or to control the addition of a component to the parenteral solution through the inner bag film wall.

2. The assembly of claim 1 wherein the random ethylenepropylene copolymer has a melt flow in the range from about 1.0 to about 5.0 g/10 min. at 230° C.

3. The assembly of claim 1 wherein the comonomer of the linear low density polyethylene component is at least one $C_4$–$C_8$ alpha-olefin.

4. The assembly of claim 1 wherein the linear low density polyethylene is a copolymer of ethylene and butene-1.

5. The assembly of claim 1 wherein the linear low density polyethylene has a melt index in the range from about 0.5 to about 5 g/10 min. at 190° C.

6. The assembly of claim 1 wherein outer film bag resin blend also contains an agent to impart improved clarity.

7. The assembly of claim 6 wherein the agent to impart improved clarity is dibenzylidene sorbitol in amounts from about 0.1 to about 2 wt % based on the total polymer weight.

8. The assembly of claim 1 wherein said substance is water in sufficient quantity, to inhibit removal of water in vapor form from the parenteral solution.

9. The assembly of claim 1 wherein said parenteral solution is blood platelets and said substance is an oxygen generating compound in sufficient quantity to add oxygen through the inner bag film wall to the blood platelets.

10. The assembly of claim 1 wherein said parenteral solution is blood platelets and said substance is a carbon dioxide absorber in sufficient quantity to remove carbon dioxide from the blood platelets through the inner bag film wall.

11. The assembly of claim 1 wherein said material is enclosed within a sealed pouch positioned in the space between the inner and outer bag and at least one wall of said pouch is permeable to vapors and gases but resistant to liquid permeability.

12. The assembly of claim 1 where the outer film bag resin also contains from about 2 to about 15 wt % of a high density polyethylene homopolymer having a density of at least 0.945 gm/cc.

* * * * *